(12) United States Patent
Pyun et al.

(10) Patent No.: US 10,894,863 B2
(45) Date of Patent: Jan. 19, 2021

(54) CATHODE MATERIALS FOR LI—S BATTERIES

(71) Applicant: ARIZONA BOARD OF REGENTS ON BEHALF OF THE UNIVERSITY OF ARIZONA, Tucson, AZ (US)

(72) Inventors: Dong-Chul Pyun, Tucson, AZ (US); Nicholas George Pavlopoulos, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 396 days.

(21) Appl. No.: 15/829,248

(22) Filed: Dec. 1, 2017

(65) Prior Publication Data

US 2018/0079865 A1    Mar. 22, 2018

Related U.S. Application Data

(63) Continuation-in-part of application No. 15/287,118, filed on Oct. 6, 2016, which is a continuation of
(Continued)

(51) Int. Cl.
*C01G 39/06* (2006.01)
*C08G 75/16* (2006.01)
(Continued)

(52) U.S. Cl.
CPC ............ *C08G 75/16* (2013.01); *A01N 41/12* (2013.01); *A01N 59/02* (2013.01); *A61K 31/795* (2013.01);
(Continued)

(58) Field of Classification Search
CPC .......... C01G 41/00; C01G 39/06; C01G 1/12; C08K 2003/3009; C08K 3/30; C01B 19/04
See application file for complete search history.

(56) References Cited

U.S. PATENT DOCUMENTS 2,779,761 A    1/1957  Kibler
2,989,513 A    6/1961  Hendry et al.
(Continued)

FOREIGN PATENT DOCUMENTS

CN    104713968 A1    6/2015
EP    0806451 A1    11/1997
(Continued)

OTHER PUBLICATIONS

Bielawski. NPG Asia Materials (2013) 5, e64; doi:10.1038/am.2013.46; published online Sep. 27, 2013.*
(Continued)

*Primary Examiner* — Michael A Salvitti
(74) *Attorney, Agent, or Firm* — Nguyen Tarbet LLC (57) ABSTRACT

Compositions and methods of producing composite materials for use as a cathode in electrochemical cells. Elemental sulfur is mixed with tungsten sulfide ($WS_2$) to form a composite mixture. Organic comonomers may be added to the composite mixture. The composite mixture is reacted to form the composite material. Electrochemical cells with cathodes containing the composite material demonstrated improved battery performance.

15 Claims, 4 Drawing Sheets
(4 of 4 Drawing Sheet(s) Filed in Color)

Related U.S. Application Data application No. 14/622,429, filed on Feb. 13, 2015, now Pat. No. 9,567,439.

(60) Provisional application No. 62/428,653, filed on Dec. 1, 2016, provisional application No. 62/039,561, filed on Aug. 20, 2014, provisional application No. 62/039,588, filed on Aug. 20, 2014, provisional application No. 62/017,750, filed on Jun. 26, 2014, provisional application No. 61/940,102, filed on Feb. 14, 2014.

(51) Int. Cl.
| | | |
|---|---|---|
| H01M 4/60 | (2006.01) | |
| H01M 10/052 | (2010.01) | |
| C01B 17/96 | (2006.01) | |
| C08L 81/04 | (2006.01) | |
| C08J 3/28 | (2006.01) | |
| A61K 31/795 | (2006.01) | |
| A01N 59/02 | (2006.01) | |
| A01N 41/12 | (2006.01) | |
| C01B 3/04 | (2006.01) | |
| H01M 4/36 | (2006.01) | |
| H01M 4/38 | (2006.01) | |
| H01M 4/58 | (2010.01) | |
| H01M 4/62 | (2006.01) | |
| C08G 75/14 | (2006.01) | |

(52) U.S. Cl.
CPC .............. *C01B 3/042* (2013.01); *C01B 17/96* (2013.01); *C08J 3/28* (2013.01); *C08L 81/04* (2013.01); *H01M 4/364* (2013.01); *H01M 4/38* (2013.01); *H01M 4/5815* (2013.01); *H01M 4/606* (2013.01); *H01M 4/62* (2013.01); *H01M 10/052* (2013.01); *C08G 75/14* (2013.01); *C08J 2381/04* (2013.01); *C08L 2201/52* (2013.01); *H01M 4/382* (2013.01); *Y02T 10/70* (2013.01)

(56) References Cited

U.S. PATENT DOCUMENTS

| | | | |
|---|---|---|---|
| 3,251,797 A | 5/1966 | De Pugh et al. | |
| 3,290,266 A | 12/1966 | Barnes et al. | |
| 3,542,701 A | 11/1970 | van Raamsdonk | |
| 3,563,962 A | 2/1971 | Mirviss | |
| 3,767,613 A | 10/1973 | Dix et al. | |
| 3,892,686 A | 7/1975 | Woo | |
| 4,000,347 A | 12/1976 | Ranney et al. | |
| 4,094,751 A | 6/1978 | Nozik | |
| 4,238,585 A | 12/1980 | Bertozzi | |
| 4,346,191 A | 8/1982 | Blount | |
| 4,382,846 A | 5/1983 | Gratzel et al. | |
| 4,568,435 A | 2/1986 | Shelnutt | |
| 4,606,798 A | 8/1986 | Sasse et al. | |
| 4,671,896 A | 6/1987 | Hasegawa et al. | |
| 4,749,347 A | 6/1988 | Valavaara | |
| 4,752,507 A | 6/1988 | Johansson et al. | |
| 4,833,048 A | 5/1989 | DeJonghe et al. | |
| 5,115,060 A | 5/1992 | Grey | |
| 5,121,329 A | 6/1992 | Crump | |
| 5,279,910 A | 1/1994 | Sasaki et al. | |
| 5,371,176 A | 6/1994 | Bezwada et al. | |
| 5,362,493 A | 11/1994 | Skotheim et al. | |
| 5,811,470 A | 9/1998 | Prindle et al. | |
| 5,919,587 A * | 7/1999 | Mukherjee | H01B 1/12 429/213 |
| 5,929,202 A | 7/1999 | Arita et al. | |
| 6,011,094 A | 1/2000 | Planche et al. | |
| 6,072,026 A | 6/2000 | Kawase et al. | |
| 6,111,030 A | 8/2000 | Hartman et al. | |
| 9,306,218 B2 * | 4/2016 | Pyun | H01M 4/382 |
| 9,463,597 B2 | 10/2016 | Van De Vrie et al. | |
| 9,567,439 B1 | 2/2017 | Pyun et al. | |
| 2001/0047043 A1 | 11/2001 | Okoroafor et al. | |
| 2001/0047403 A1 | 11/2001 | Okoroafor et al. | |
| 2002/0039680 A1 | 4/2002 | Hwang et al. | |
| 2006/0239882 A1 * | 10/2006 | Seo | C01G 55/00 423/263 |
| 2007/0010600 A1 | 1/2007 | Goodman et al. | |
| 2007/0253772 A1 | 11/2007 | Kubo et al. | |
| 2008/0038645 A1 * | 2/2008 | Kolosnitsyn | H01M 4/40 429/338 |
| 2010/0029163 A1 | 2/2010 | Ogle et al. | |
| 2011/0245360 A1 | 10/2011 | Hahn et al. | |
| 2011/0263755 A1 | 10/2011 | Mohamed et al. | |
| 2012/0264837 A1 | 10/2012 | Eberstaller et al. | |
| 2013/0040197 A1 | 2/2013 | Liu et al. | |
| 2013/0064904 A1 | 3/2013 | Gojon-Romanillos et al. | |
| 2014/0110881 A1 | 4/2014 | Keledjian et al. | |
| 2014/0199592 A1 | 7/2014 | Pyun et al. | |
| 2015/0203638 A1 | 7/2015 | Sivanandan et al. | |
| 2015/0361241 A1 * | 12/2015 | Loomis | H05K 1/167 174/254 |
| 2018/0079865 A1 * | 3/2018 | Pyun | C08L 81/04 |
| 2018/0105649 A1 | 4/2018 | Pyun et al. | |
| 2018/0301694 A1 * | 10/2018 | Sung | H01M 4/136 |

FOREIGN PATENT DOCUMENTS

| | | |
|---|---|---|
| EP | 1882713 A1 | 1/2008 |
| EP | 2093605 A1 | 8/2009 |
| EP | 2896644 A1 | 7/2015 |
| GB | 1203577 A | 8/1970 |
| GB | 1516554 A | 7/1978 |
| WO | WO1995018652 A1 | 7/1995 |
| WO | WO2007076067 A3 | 7/2007 |
| WO | WO2009158385 A | 12/2009 |
| WO | WO2013023216 A1 | 2/2013 |
| WO | WO2013155038 A1 | 10/2013 |
| WO | WO2014052255 A1 | 4/2014 |
| WO | WO2014179100 A1 | 11/2014 |
| WO | WO2015123552 A1 | 8/2015 |

OTHER PUBLICATIONS

Ding et al. Photoelectrocatalytic Water Splitting: Significance of Cocatalysts, Electrolyte, and Interfaces. ACS Catal. 2017, 7, 675-688.

Chung, W.J. et al, "Elemental Sulfur as a Reactive Medium for Gold Nanoparticles and Nanocomposite Materials", Angewandte Chemie International Edition, 2011, 50, 11409-11412.

Colquhoun, Howard M., "Materials that heal themselves", Nature Chemistry, Jun. 2012, vol. 4, 435-436.

Yang, Ying and Urban Marek W., "Self-healing polymeric materials", Chem. Soc. Rev., 2013, 42, 7446-7467.

Hasegawa, Urara and Van Der Vlies, André J., "Design and Synthesis of Polymeric Hydrogen Sulfide Donors", Bioconjugate Chemistry, 2014, 25 (7), 1290-1300.

Foster, Jeffrey C., et al, "S-Aroylthiooximes: A Facile Route to Hydrogen Sulfide Releasing Compounds with Structure-Dependent Release Kinetics", Organic Letters. 2014, 16, 1558-1561.

Wurthner, F., "Perylene bisimide dyes as versatile building blocks for functional supramolecular architectures", Chem. Commun. 2004, 1564-1579.

Chung, W.-. et al., "The use of elemental sulfur as an alternative feedstock for polymeric materials", Nature Chemistry 2013, vol. 5, 518-524.

Simmonds, A.G. et al., "Inverse Vulcanization of Elemental Sulfur to Prepare Polymeric Electrode Materials for Li—S Batteries", ACS Macro Lett. 2014, 3, 229-232.

Liu, G. et al., "α-Sulfur Crystals as a Visible-Light-Active Photocatalyst", J. Am. Chem. Soc. 2012, 134, 9070-9073.

Asmus, K.-D., "Pulse Radiolysis Methodology", Methods in Enzymology 1984, 105, 167-178.

(56) References Cited

OTHER PUBLICATIONS

Nishide, et al., "Toward Flexible Batteries", (2008) Science, vol. 319, 737-738.
Nishide, et al., "Emerging N-Type Redox-Active Radical Polymer for a Totally Organic Polymer-Based Rechargeable Battery", (2009), Adv Mater, 21, 1627-1630.
Tarascon, et al., "Key challenges in future Li-battery research", (2010) Phil Trans R Soc A, 368, 3227.
Rotinjanz, et al. (1908) Z. Physik Chem, 62, 609.
Bacon, et al., "The Viscosity of Sulfur", (1943) J Am Chem Soc, 65, 639.
Eyring, et al., "The Properties of Liquid Sulfur", (1943) J Am Chem 65, 648.
Tobolsky, A. V. et al., "Equilibrium Polymerization of Sulfur", Am. Chem. Soc.1959, 81, 780.
Penczek, et al. (1974) Nature, 273, 738.
Nazar et al., "A highly ordered nanostructured carbon-sulphur cathode for lithium-sulphur batteries", Nature Mater. 2009, 8, 500-506.
Scrosati, et al., "A High-Performance Polymer Tin Sulfur Lithium Ion Battery", Angew. Chem. Int. Ed. 2010, 49, 2371-2374.
Then, et al., J. Phys. Chem. C 2011, 115, 6057-6063.
Yang, et al., ACS Nano 2011, 5, 9187-9193.
Bartlett, et al., (1956) J Am Chern Soc, 78, 3710.
McGrath, et al. (2006) Polymer, 47, 4042.
Ueda et al., (2009) J Mater Chem, 19, 8907.
Trofimov, et al. (2002) "Sulfur-rich copolymers of sulfur with 5-vinylbicyclo hept-2-ene and tricyclo deca-3,8-diene as prospective cathode materials for lithium cells," Sufur Letters, 25: 219-227.
Ning, et al., (2004) "Novel cathode material based on chloropolystyrene," PMSE Preprints, American Chemical Society 90: 396-397.
Wang, et al., Nano Lett. 2011, 11, 2644-2647.
Zheng, et al., Nano Lett. 2011, 11, 4462-4467.
Li, et al., Proc. Nail. Acad. Sci. U.S.A. 2013, 110, 7148-7153.
Zheng, et al., Nano Lett. 2013, 13, 1265-1270.
Zhou, et al., ACS Nano 2013, 7, 8801-8808.
Seh, et al., Nat. Commun. 2013, 4.
Li, et al., Nano Lett. 2013, 13, 5534.
Liu, et al., Nat. Nanolech. 2014, 9, 187.
Pyun, J. Angew. Chem Int. Ed., 2011, 50, 11409-11412.
Woo et al. Nature Chemistry. Jun. 2013. vol. 5, pp. 518-524. Published online Apr. 14, 2013.
Suzuki et al. Hydrogen generation using water-insoluble polymer-bound ruthenium(ii) Complexes. Chemical Communications, 1997, Issue 2, p. 227.
Suzuki et al. Photoinduced hydrogen generation from water-insoluble polymer photosensitizer films. Polymer, 1998, vol. 39, Issue 8, p. 1539-1543.
Suzuki et al. Photoinduced hydrogen generation using polymer photosensitizers. Macromolecular Chemistry and Physics, Jun. 1998, vol. 199, Issue 6.
Wang et al. A metal-free polymeric photocatalyst for hydrogen production from water under visible light. Nature Materials 8, 76-80 (2009).
Goldsmith et al. Discovery and High-Throughput Screening of Heteroleptic Iridium Complexes for Photoinduced Hydrogen Production. J. Am. Chem. Soc., 2005, 127 (20), pp. 7502-7510.
Tinker et al. Visible Light Induced Catalytic Water Reduction without an Electron Relay. Chemistry—A European Journal, 2007, vol. 13, Issue 31, pp. 8726-8732.
Happ et al. Towards Hydrogen Evolution Initiated by LED Light: 2-(1 H-1,2,3-Triazol-4-yl)pyridine containing Polymers as Photocatalyst. Macromolecular Rapid Communications, Apr. 2015, vol. 36, Issue 7, 671-677.
Aguirre De Carcer et al. Active-Site Models for Iron Hydrogenases: Reduction Chemistry of Dinuclear Iron Complexes. Inorg. Chem., 2006, 45 (20), pp. 8000-8002.
Alongia et al. Caseins and hydrophobins as novel green flame retardants for cotton fabrics. Polymer Degradation and Stability vol. 99, Jan. 2014, pp. 111-117.
Beom-Young Ryu and Todd Emrick. Thermally Induced Structural Transformation of Bisphenol-1,2,3-triazole Polymers: Smart, Self-Extinguishing Materials. Angew. Chem. Int. Ed. 2010, 49, 9644-9647.
Laufer et al. Clay-Chitosan Nanobrick Walls: Completely Renewable Gas Barrier and Flame-Retardant Nanocoatings. ACS Appl. Mater Interfaces 2012, 4, 1643-1649.
Laufer et al. Exceptionally Flame Retardant Sulfur-Based Multilayer Nanocoating for Polyurethane Prepared from Aqueous Polyelectrolyte Solutions. ACS Macro Lett., 2013, 2 (5), pp. 361-365.
Li et al. Intumescent All-Polymer Multilayer Nanocoating Capable of Extinguishing Flame on Fabric. Adv. Mater. 2011, 23, 3926-3931.
Swenson, M. Synthesis and Characterization of [Fe Fe) Hydrogenase Mimics. The University of Arizona, 2013, pp. 1-157 online), [retrieved on Jan. 19, 2018]. Retrieved from the Internet <http://arizona.openrepository.com/arizona/handle/1 0150/294029>.

* cited by examiner

CATHODE MATERIALS FOR LI—S BATTERIES

CROSS REFERENCE

This application is a non-provisional and claims benefit of U.S. Provisional Patent Application No. 62/428,653 filed Dec. 1, 2016, the specification(s) of which is/are incorporated herein in their entirety by reference.

This application is a continuation-in-part and claims benefit of U.S. patent application Ser. No. 15/287,118 filed Oct. 6, 2016, which is a continuation and claims benefit of U.S. patent application Ser. No. 14/622,429 filed Feb. 13, 2015, now U.S. Pat. No. 9,567,439, which claims priority to U.S. Provisional Patent Application No. 62/039,588 filed Aug. 20, 2014, U.S. Provisional Patent Application No. 62/039,561 filed Aug. 20, 2014, U.S. Provisional Patent Application No. 62/017,750 filed Jun. 26, 2014, and U.S. Provisional Patent Application No. 61/940,102 filed Feb. 14, 2014, the specification(s) of which is/are incorporated herein in their entirety by reference.

GOVERNMENT SUPPORT

This invention was made with government support under Grant No. CHE1305773 awarded by NSF. The government has certain rights in the invention.

FIELD OF THE INVENTION

The present invention relates to sulfur-based cathode materials for Li—S batteries, in particular, to cathode materials prepared from a reaction of elemental liquid sulfur, vinylic comonomers, and $WS_2$ particles.

BACKGROUND OF THE INVENTION

An incredible abundance of elemental sulfur, nearly 7-million tons is generated as a waste byproduct from hydrodesulfurization of crude petroleum feedstocks, which converts alkanethiols and other (organo) sulfur compounds into $S_8$ as described in Chung and which is hereby incorporated herein by reference in its entirety. Before the invention of the inverse vulcanization process, there were only a limited number of synthetic methods available to utilize and modify elemental sulfur. Current industrial utilization of elemental sulfur is centered around sulfuric acid, agrochemicals, and vulcanization of rubber. For example, elemental sulfur is used primarily for sulfuric acid and ammonium phosphate fertilizers, where the rest of the excess sulfur is stored as megaton-sized, above ground sulfur towers.

While sulfur feedstocks are plentiful, sulfur is difficult to process. In its original form, elemental sulfur consists of a cyclic molecule having the chemical formulation $S_8$. Elemental sulfur is a brittle, intractable, crystalline solid having poor solid state mechanical properties, poor solution processing characteristics, and there is a limited slate of synthetic methodologies developed for it. Hence, there is a need for the production of new materials that offers significant environmental and public health benefits to mitigate the storage of excess sulfur in powder, or brick form.

Elemental sulfur has been explored for use in lithium-sulfur electrochemical cells. Sulfur can oxidize lithium when configured appropriately in an electrochemical cell, and is known to be a very high energy-density cathode material. The poor electrical and electrochemical properties of pure elemental sulfur, such as low cycle stability and poor conductivity) have limited the development of this technology. For example, one key limitation of lithium-sulfur technology is the ability to retain high charge capacity for extended numbers of charge-discharge cycles ("cycle lifetimes"). Cells based on present lithium ion technology has low capacity (180 mAh/g) but can be cycled for 500-1000 cycles. Lithium-sulfur cells based on elemental sulfur have very high initial charge capacity (in excess of 1200 mAh/g, but their capacity drops to below 400 mAh/g within the first 100-500 cycles. Hence, the creation of novel copolymer materials from elemental sulfur feedstocks would be tremendously beneficial in improving sustainability and energy practices. In particular, improved battery technology and materials that can extend cycle lifetimes while retaining reasonable charge capacity will significantly impact the energy and transportation sectors and further mitigate US dependence on fossil fuels.

WO2015123552A1 of Pyun teaches Li—S batteries fabricated with a $MoS_2/S_8$ cathode material. These Li—S batteries were able to survive to 1000 charge-discharge cycles while retaining charge capacities around about 400 mAh/g. However, the cathode material required a high content of $MoS_2$ of about 50 wt %, and thus only allowed for lower sulfur loadings of about 50 wt %.

The present invention features an improved cathode material utilizing a 2-D inorganic material that inherently possesses high Li-ion conductivity and transport properties, and also enables the use of higher contents of the active sulfur phase.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

According to some embodiments, the subject disclosure features a composite material comprising at least about 50 wt % sulfur derived from $S_8$, and about 5-50 wt % tungsten sulfide ($WS_2$). The composite material may further comprise about 5-10 wt % of one or more comonomers, such as 1,3-diisopropenylbenzene.

In one embodiment, the invention features an active material for use in a battery electrode, e.g. cathode, may comprise said composite material. Another embodiment of the invention features electrochemical cells comprising an anode comprising lithium, a cathode comprising the composite material, and a non-aqueous electrolyte interposed between the cathode and the anode.

Yet a further embodiment of the invention features a method of producing the composite material for use as a cathode in an electrochemical cell. The method may comprise providing about 50 wt % elemental sulfur, adding about 5-50 wt % tungsten sulfide ($WS_2$) to the elemental sulfur, thereby forming a composite mixture, and heating and mixing the composite mixture, thereby forming the composite material. The method may further comprise adding one or more comonomers to the composite mixture.

One of the unique and inventive technical features of the present invention is the use of an inorganic 2-D material with good Li-ion transporting properties in a composite material that can be prepared into a novel and inexpensive cathode material. Without wishing to limit the invention to any theory or mechanism, it is believed that the technical feature of the present invention advantageously improves Li—S battery performance by retaining higher charge capacities while also increasing sulfur loading. None of the presently known prior references or work has the unique inventive technical feature of the present invention.

BRIEF DESCRIPTION OF THE DRAWINGS

This patent application contains at least one drawing executed in color. Copies of this patent or patent application publication with color drawing(s) will be provided by the Office upon request and payment of the necessary fee. The features and advantages of the present invention will become apparent from a consideration of the following detailed description presented in connection with the accompanying drawings in which.

DESCRIPTION OF PREFERRED EMBODIMENTS

As used herein, sulfur can be provided as elemental sulfur, for example, in powdered form. Under ambient conditions, elemental sulfur primarily exists in an eight-membered ring form ($S_8$) which melts at temperatures in the range of 120° C.-130° C. and undergoes an equilibrium ring-opening polymerization (ROP) of the $S_8$ monomer into a linear polysulfane with diradical chain ends. As the person of skill in the art will appreciate, while $S_8$ is generally the most stable, most accessible and cheapest feedstock, many other allotropes of sulfur can be used (such as other cyclic allotropes, derivable by melt-thermal processing of $S_8$). Any sulfur species that yield diradical or anionic polymerizing species when heated as described herein can be used in practicing the present invention.

As used herein, a "styrenic comonomer" is a monomer that has a vinyl functional group. The styrenic comonomer may comprise a styrene and at least one reactive functional group. As known to one of ordinary skill in the art, a styrene is a derivative of benzene ring that has a vinylic moiety. The sulfur diradicals can link to the vinylic moieties of the styrenic commoners to form the sulfur-styrenic polymer. In certain embodiments, the reactive functional group may be a halogen, an alkyl halide, an alkyl, an alkoxy, an amine, or a nitro functional group. Non-limiting examples of styrenic comonomers include bromostyrene, chlorostyrene, (trifluoromethyl)styrene, fluorostyrene, vinylaniline, acetoxystyrene, methoxystyrene, ethoxystyrene, methylstyrene, nitrostyrene, vinylbenzoic acid, vinylanisole, and vinylbenzyl chloride.

As used herein, an ethylenically unsaturated monomer is a monomer that contains an ethylenically unsaturated functional group (i.e. double bond). The term "ethylenically unsaturated" may be used interchangeably with the term "unsaturated". One of ordinary skill in the art will understand that "unsaturated" refers to the C=C functional group. The term "ethylenically unsaturated monomer" does not include compounds in which the ethylenic unsaturation is part of a long chain alkyl moiety (e.g. unsaturated fatty acids such as oleates, and unsaturated plant oils).

Non-limiting examples of ethylenically unsaturated monomers include vinyl monomers, acryl monomers, (meth)acryl monomers, unsaturated hydrocarbon monomers, and ethylenically-terminated oligomers. Examples of such monomers include, generally, mono- or polyvinylbenzenes, mono- or polyisopropenylbenzenes, mono- or polyvinyl(hetero)aromatic compounds, mono- or polyisopropenyl(hetero)-aromatic compounds, acrylates, methacrylates, alkylene di(meth)acrylates, bisphenol A di(meth)acrylates, benzyl (meth)acrylates, phenyl(meth)acrylates, heteroaryl (meth)acrylates, terpenes (e.g., squalene) and carotene. In some embodiments, non-limiting examples of ethylenically unsaturated monomers that are non-homopolymerizing include allylic monomers, isopropenyls, maleimides, norbornenes, vinyl ethers, and methacrylonitrile. In other embodiments, the ethylenically unsaturated monomers may include a (hetero)aromatic moiety such as, for example, phenyl, pyridine, triazine, pyrene, naphthalene, or a polycyclic (hetero)aromatic ring system, bearing one or more vinylic, acrylic or methacrylic substituents. Examples of such monomers include benzyl (meth)acrylates, phenyl (meth)acrylates, divinylbenzenes (e.g., 1,3-divinylbenzene, 1,4-divinylbenzene), isopropenylbenzene, styrenics (e.g., styrene, 4-methylstyrene, 4-chlorostyrene, 2,6-dichlorostyrene, 4-vinylbenzyl chloride), diisopropenylbenzenes (e.g., 1,3-diisopropenylbenzene), vinylpyridines (e.g., 2-vinylpyridine, 4-vinylpyridine), 2,4,6-tris((4-vinylbenzyl) thio)-1,3,5-triazine and divinylpyridines (e.g., 2,5-divinylpyridine). In certain embodiments, the ethylenically unsaturated monomers (e.g., including an aromatic moiety) bear an amino (i.e., primary or secondary) group, a phosphine group or a thiol group. One example of such a monomer is vinyldiphenylphosphine.

As used herein, an "elemental carbon material" is a material that is primarily formed as an allotrope of carbon, with a minor amount of chemical modification. For example, graphene, graphene oxide, graphite, carbon nanotubes, fullerenes, carbon black, carbon flakes and carbon fibers are examples of elemental carbon materials. As a general guideline for the person of skill in the art, up to about 15 wt % elemental carbon material can be dispersed in sulfur at temperatures high enough such that the sulfur is molten, but low enough that significant ring opening and polysulfide polymerization does not occur (e.g., at temperatures in the range of about 120° C. to about 160° C.). Higher loadings of elemental carbon materials in sulfur can be achieved by pre-dissolution of the sulfur and dispersion of the elemental carbon material into a suitable solvent (e.g., carbon disulfide) followed by removal of the solvent under reduced pressure to yield a blended composite powder. To induce curing of the dispersed carbon, or other nanoinclusions with the sulfur matrix, direct heating of the dispersion to above 160° C. but typically below 200° C. affords a polymerized nanocomposite.

As used herein, the term "functional" in correlation with a polymer refers to functional polymers that have specified physical, chemical, biological, pharmacological, or other properties or uses that are determined by the presence of specific chemical functional groups, which are usually dissimilar to those of the backbone chain of the polymer.

As used herein, the terms "those defined above" and "those defined herein" when referring to a variable incorporates by reference the broad definition of the variable as well as any narrow and/or preferred definitions, if any.

Referring now to FIGS. 1-4, the present invention features a composite material comprising at least about 50 wt % sulfur derived from $S_8$, and about 5-50 wt % tungsten sulfide ($WS_2$). In some embodiments, $WS_2$ is dispersed in the sulfur.

In one embodiment, the composite material may comprise about 60 wt % sulfur and about 5-40 wt % $WS_2$. In another embodiment, the composite material may comprise about 70 wt % sulfur and about 5-30 wt % $WS_2$. In yet another embodiment, the composite material may comprise about 80 wt % sulfur and about 5-20 wt % $WS_2$. In a further embodiment, the composite material may comprise about 90 wt % sulfur and about 5-10 wt % $WS_2$.

According to some embodiments, the composite material may further comprise about 5-10 wt % of one or more comonomers. For example, the composite material may comprise about 10 wt % of a comonomer. Without wishing to limit the invention to a particular theory or mechanism, the one or more comonomers can polymerize with sulfur to form a sulfur copolymer. $WS_2$ may be dispersed in the sulfur copolymer and act as a filler to reinforce the sulfur copolymer composite material. Non-limiting example of the one or more comonomers may include ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, or monomers having at least one isopropenyl moiety. For example, the comonomer may be 1,3-diisopropenylbenzene.

The use of a new electroactive cathode material for a Li—S battery, namely the composite material described herein, upon discharge, generates soluble additive species in situ that co-deposit onto the cathode with lower sulfide discharge products. These additive species may be introduced into the electroactive material during the synthesis of the material, or alternatively added to the electrolyte or battery separator as a soluble species. These additive species are able to co-deposit with sulfide-containing discharge products via active electrochemical reactions, or passive non-electrochemical processes. Without wishing to limit the invention to a particular theory or mechanism, co-deposition of these additive species with sulfide discharge products onto the Li—S cathode may plasticize the electrode against mechanical fracture during battery charge-discharge cycling. Plasticization enables retention of charge capacity and improve cycle lifetime beyond 100 cycles. The electroactive material in this case is best embodied by the composite materials described herein. Upon discharge of this composite material, soluble organosulfur species are formed which function to improve Li—S batteries.

Another embodiment of the invention features an electrochemical cell. The electrochemical cell may comprise an anode comprising lithium, such as metallic lithium, a cathode comprising a composite material comprising at least about 50 wt % sulfur derived from $S_8$, and about 5-50 wt % tungsten sulfide ($WS_2$), and a non-aqueous electrolyte interposed between the cathode and the anode. The composite material can generate soluble additive species in situ upon discharge, and the soluble additive species are co-deposited with lower sulfide discharge products onto the cathode by an electrochemical reaction or a non-electrochemical reaction. In some embodiments, the lower sulfide discharge products are $Li_2S_3$, $Li_2S_2$, or $Li_2S$.

Without wishing to limit the invention to a particular theory or mechanism, the composite material is effective for providing an electrochemical cell an increased volumetric energy density. For example, the capacity of the electrochemical cell can range from about 500 to about 1400 mAh/g. Further still, the electrochemical cell can have a high retention of charge capacity at fast charge-discharge rates. In some embodiments, the C-rate is about 1 C. For example, a composite material comprising $S_8$ and $WS_2$ may provide for an electrochemical cell having fast charge-discharge rates. As another example, a composite material comprising $S_8$, $WS_2$, and a vinylic comonomer may provide for an electrochemical cell having long cycle lifetimes with higher charge capacity.

Without wishing to limit the invention to a particular theory or mechanism, the use of $WS_2$ in the composite material provides for a 2-D inorganic material that inherently possesses a high Li-ion conductivity and transport properties. In addition, higher loading of sulfur in the composite material was achieved in the present invention.

In some embodiment, the composite material may comprise about 60 wt % sulfur and about 5-40 wt % $WS_2$. In preferred embodiments, the composite material may comprise about 70 wt % sulfur and about 5-30 wt % $WS_2$. In more preferred embodiments, the composite material may comprise about 80 wt % sulfur and about 5-20 wt % $WS_2$. In further embodiments, the composite material may comprise about 90 wt % sulfur and about 5-10 wt % $WS_2$.

In some embodiments, $WS_2$ is dispersed in the sulfur. According to other embodiments, the composite material may further comprise about 5-10 wt % of one or more comonomers. Without wishing to limit the invention to a particular theory or mechanism, the one or more comonomers can polymerize with sulfur to form a sulfur copolymer. $WS_2$ is dispersed in the sulfur copolymer and acts as a filler to reinforce the sulfur copolymer composite material. Examples of the one or more comonomers include, but are not limited to, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety. For example, in one embodiment, the one or more comonomers may be 1,3-diisopropenylbenzene comonomers.

In some embodiments, the cathode may further comprise an elemental carbon material dispersed in the composite material. For example, the carbon material is at most about 5 wt %, or at most about 10 wt %, or at most about 15 wt %, or at most about 20 wt % of the cathode.

Any embodiment of the electrochemical cells may be used in electric vehicle applications, portable consumer devices portable consumer devices (e.g., Personal electronics, cameras, electronic cigarettes, handheld game consoles, and flashlights), motorized wheelchairs, golf carts, electric bicycles, electric forklifts, tools, automobile starters, and uninterruptible power supplies.

In alternative embodiments, the electrolyte and/or a separator may comprise the composite material. The composite material can generate soluble organosulfur species upon discharge. The soluble additive species are co-deposited with the lower sulfide discharge products by an electrochemical reaction or a non-electrochemical reaction.

According to some embodiments, the present invention features a method of producing a composite material for use as a cathode in an electrochemical cell. The method may comprise providing about 50 wt % elemental sulfur, adding about 5-50 wt % tungsten sulfide ($WS_2$) to the elemental sulfur, thereby forming a composite mixture, and heating and stirring the composite mixture for a period of time, thereby forming the composite material.

In some embodiments, prior to adding $WS_2$, the elemental sulfur can be melted at a temperature of about 120-140° C. to form a liquid phase. In other embodiments, the composite mixture of elemental sulfur and $WS_2$ may be heated together to a temperature of about 160° C. to 200° C. to initiate the reaction process. In preferred embodiments, the composite mixture is rapidly stirred at a rate of about 500-800 rpm to achieve homogeneity of the mixture.

In some embodiments, the period of time is determined by selecting the shortest time from the following: 1) when vitrification occurs; or 2) when the composite mixture has been heated and stirred for about 60-70 minutes. As known to one skilled in the art, vitrification is a process where a substance is converted to a glassy form, such as a non-crystalline amorphous solid, usually by heating and fusion. In further embodiments, when the composite mixture has been heated and stirred for about 60-70 minutes, the composite mixture is removed from the heat source and allowed to cool, thereby forming the composite material in solid form.

In other embodiments, the method may further comprise adding about 5-10 wt % of one or more comonomers to the composite mixture. Examples of the one or more comonomers include ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety. In one embodiment, the one or more comonomers may be 1,3-diisopropenylbenzene comonomers.

Figure 1:
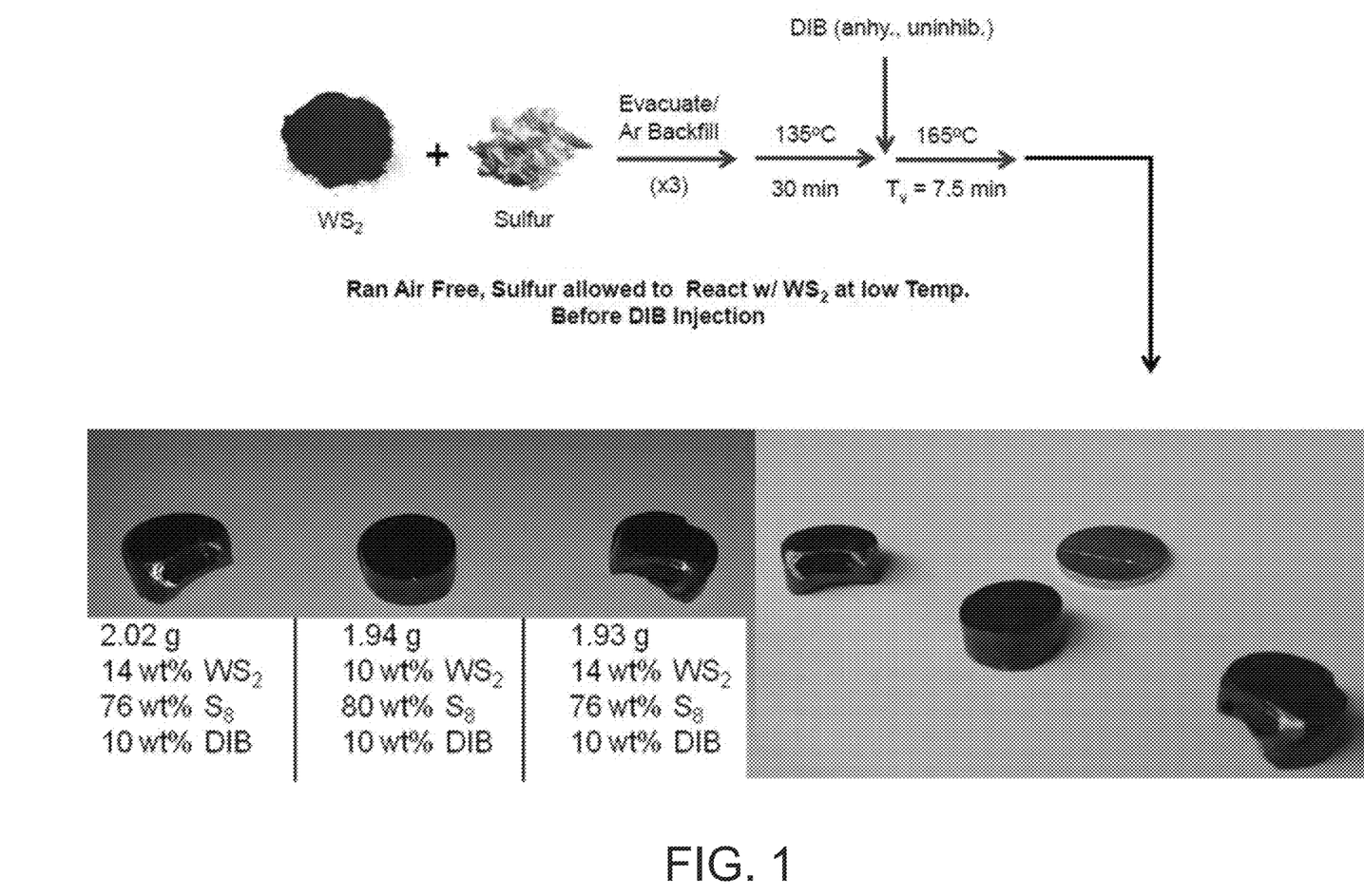
FIG. 1 shows a non-limiting example of a reaction scheme for preparing the composite material of the present invention. Non-limiting examples of the composite material having varying compositions are also shown.

Referring to FIG. 1, in some embodiments, the comonomers may be added to the composite mixture of the elemental sulfur and $WS_2$ after stirring and heating the composite mixture to a temperature of about 120-140° C., e.g. 135° C., for a first period of time, e.g. about 20-40 minutes. The composite mixture with the comonomers may then be further heated to a temperature of about 160° C. to 200° C. and mixed for a second period of time. The second period of time may be determined by selecting the shortest time from the following: 1) when vitrification occurs; or 2) when the mixture has been heated and stirred for a combined time period of about 60-70 minutes. In other embodiments, the mixture may be processed for longer than 70 minutes.

Figure 2:
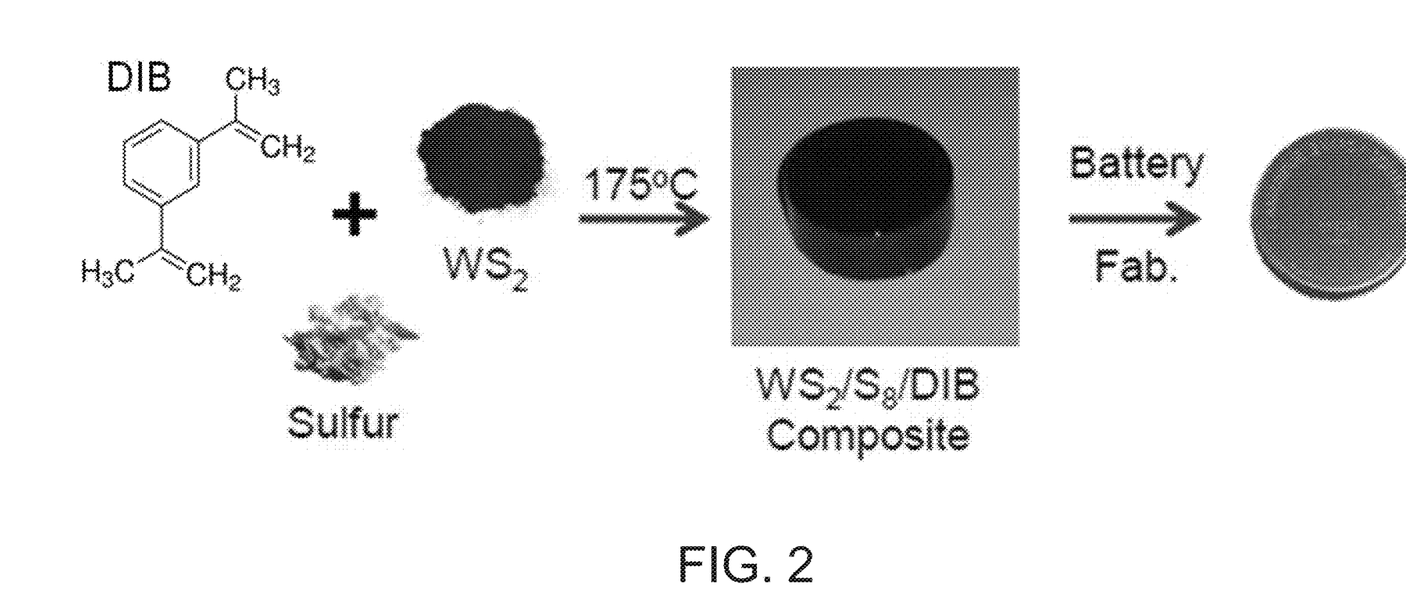
FIG. 2 shows another non-limiting example of a reaction scheme for preparing the composite material, which may then be fabricated for use in an electrochemical cell, such as a battery.

Referring to FIG. 2, in another embodiment, the comonomers may be added along with the elemental sulfur and tungsten sulfide prior to heating and stirring. The composite mixture may then be heated to a temperature of about 160° C. to 200° C. and mixed for a period of time. The period of time may be determined by selecting the shortest time from the following: 1) when vitrification occurs; or 2) when the composite mixture has been heated and stirred for about 60-70 minutes. In some embodiments, the composite mixture may be processed for longer than 70 minutes.

In further embodiments, the elemental sulfur may first be heated to a temperature of about 120-140° C. so as to form molten sulfur. Subsequently, the tungsten sulfide and comonomers may be added, simultaneously or in sequence, to the molten sulfur. The composite mixture may then be heated to a temperature of about 160° C. to 200° C. and mixed for a period of time. Again, the period of time may be determined by selecting the shortest time from the following: 1) when vitrification occurs; or 2) when the composite mixture has been heated and stirred for about 60-70 minutes. In other embodiments, the composite mixture may be processed for longer than 70 minutes.

EXAMPLES

The following are non-limiting examples of preparing the composites of the present invention. These examples are understood to be for illustrative purposes only, and that substitutes and/or equivalents are within the scope of the invention.

In general, elemental sulfur was melted at a temperature >120° C. to form a liquid sulfur. Solid $WS_2$ particulates were added and dispersed into the liquid sulfur. Vinylic comonomers were added to the mixture to solidify the material via formation of sulfur-copolymer composite reinforced with $WS_2$ fillers. In other embodiments, the method may be performed as a one-step, one-pot process.

Example 1

Synthesis of 10 wt % Tungsten Sulfide ($WS_2$)/10 wt % 1,3-Diisopropenylbenzene (DIB)/80 wt % Sulfur ($S_8$) Battery Material (2 g Scale)

Referring to FIG. 1, a composite was prepared utilizing a 4 dram glass vial equipped with a ½" Teflon coated stirbar. To the vessel was added elemental sulfur (1.600 g, 4.99×$10^{-2}$ mol) followed by tungsten sulfide powder (0.200 g, 8.07×$10^{-4}$ mol). The vial was sealed with a rubber septum and evacuated for 5 minutes, followed by backfilling with argon. This procedure was repeated twice for a total of three vacuum/backfill cycles, in order to remove any adventitious moisture from the system and to prevent high temperature oxidation of tungsten sulfide. Subsequently, the contents of the vial were homogenized via vortex mixing to result in a light grey powder, before being mixed at 135° C. for 2 minutes at 100 RPM, then at 750 RPM for 18 minutes once the sulfur has melted. DIB (0.200 g, 0.216 mL, 1.26×$10^{-3}$ mol) was added to the resulting homogeneous black dispersion at 135° C. under argon, and the mixture was allowed to homogenize for 2 minutes at 750 RPM. The vial was then transferred to an oil bath thermostated at 165° C., where the black dispersion was allowed to heat with rapid stirring (750 RPM) until vitrification was observed (about 7.5 min), which yielded a black, homogeneous, rubbery solid.

Example 2

Synthesis of 50 wt % $WS_2$/50 wt % Sulfur Battery Material (2 g Scale)

A composite was prepared utilizing a 4 dram glass vial equipped with a ½" Teflon coated stirbar. To the vessel was added elemental sulfur (1.000 g, 3.12×$10^{-2}$ mol) followed by tungsten sulfide powder (1.000 g, 4.03×$10^{-3}$ mol). The vial was sealed with a rubber septum and evacuated for 5 minutes, followed by backfilling with argon. This procedure was repeated twice for a total of three vacuum/backfill cycles, in order to remove any adventitious moisture from the system and to prevent high temperature oxidation of tungsten sulfide. Subsequently, the contents of the vial were homogenized via vortex mixing to result in a dark grey powder, before being mixed at 135° C. for 20 minutes at 750 RPM. Stirring at high rate was found to be necessary in order to result in a homogeneous composite. The vial was then transferred to an oil bath thermostated at 165° C., where the black dispersion was allowed to heat with rapid stirring (750 RPM) until vitrification was observed (about 15 min), yielding a black, homogeneous, brittle solid.

Example 3

General Synthesis of $WS_2$/Sulfur Battery Materials (2 g Scale)

A variety of $WS_2/S_8$ battery materials were found to be accessible following the procedure utilized for the 50/50 wt % composite material, ranging from 10/90 wt % $WS_2/S_8$, 20/80 wt % $WS_2/S_8$, 30/70 wt % $WS_2/S_8$, and 40/60 wt % $WS_2/S_8$. For each of these samples, thick black inks were observed after 15 minutes of reaction. Decreasing wt % of $WS_2$ in the composite was observed to track with increased vitrification time, with 40/60 wt % $WS_2/S_8$ samples vitrifying at 20 minutes, whereas 30/70 wt % $WS_2/S_8$ samples vitrified at 1 hour time points to form characteristic black, homogeneous, brittle solids. Interestingly, vitrification was not observed for 20/80 wt % $WS_2/S_8$ samples and 10/90 wt % $WS_2/S_8$ samples after 1 hour of reaction time, but solidification to form black, homogeneous, brittle solids were observed for each after removing from the oil bath and allowing to cool naturally to room temperature.

Example 4

Synthesis of Coin Cell Batteries

Coin cell batteries were fabricated from $WS_2/S_8$/DIB composite material by first preparing a mixture of electroactive cathode material ($WS_2/S_8$/DIB), conductive carbon, and polyethylene. This mixture was ball-milled in chloroform to result in a black slurry, which was subsequently doctor-blade coated onto conductive carbon-coated aluminum foil and allowed to dry, resulting in a conductive cathode film. Out of this film, circular cathodes of 1 $cm^2$ total area were punched. These cathodes were then assembled into a 2032-coin cell with a polypropylene separator, lithium foil anode, and supporting electrolyte mixture comprised of lithium bis(trifluoromethane)-sulfonimide, lithium nitrate in 1:1 v/v 1,3-dioxolane:1,2-dimethoxyethane.

Example 5

Cycling Experiment

Figure 3:
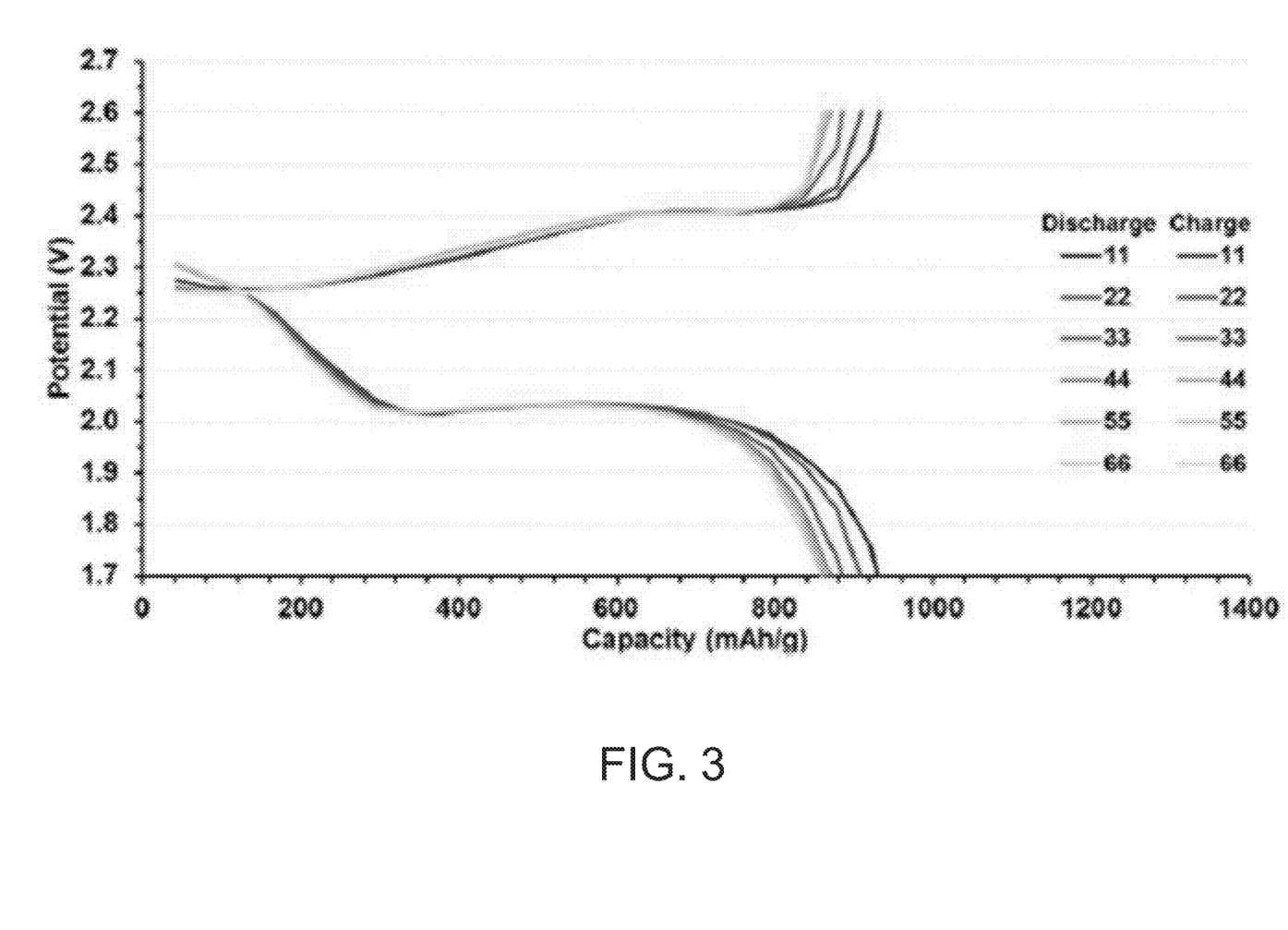
FIG. 3 shows charge-discharge profiles at various cycles of a Li—S battery having the $WS_2/S_8$ composite as the cathode active material.
Figure 4:
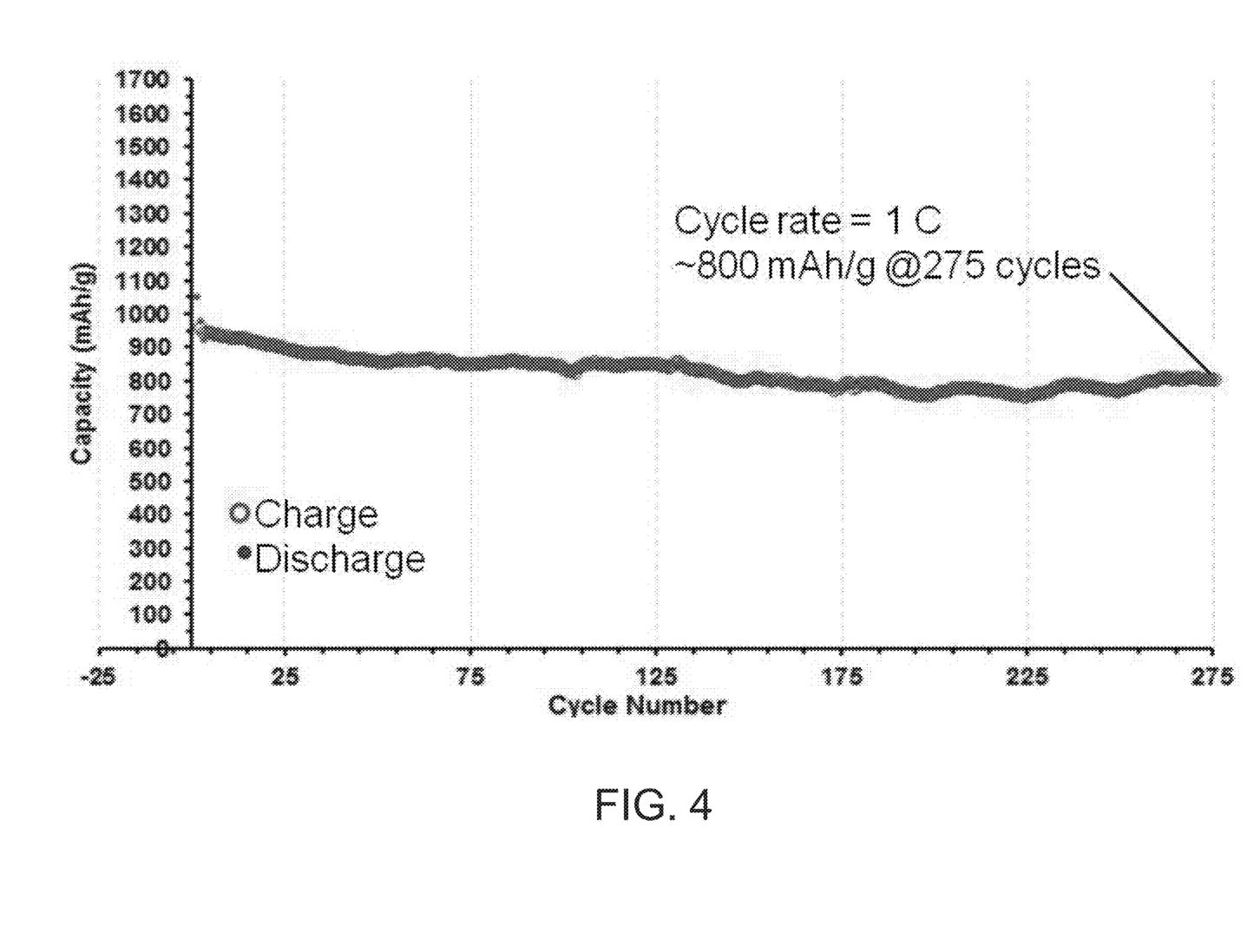
FIG. 4 shows an extended cycling experiment with a cycle rate of 1 C for 275 cycles of a Li—S battery having the $WS_2/S_8$ composite as the cathode active material.

Referring to FIGS. 3 and 4, the prepared coin cell batteries were then cycled from 2.6 V to 1.7 V, and the $WS_2/S_8$/DIB composites were found to result in high initial specific capacity (about 900 mAh/$g_{sulfur}$). In FIG. 4, cycling experiments were run at a charge/discharge rate of 1 C, equivalent to a single charge or discharge cycle per hour. At this cycle rate, a high initial capacity of about 900 mAh/g of active material was observed. By 275 cycles, about 85% of this initial capacity was retained, demonstrating the long-term cycle life of the prepared composites.

As used herein, the term "about" refers to plus or minus 10% of the referenced number.

The disclosures of the following U.S. Patents are incorporated in their entirety by reference herein: U.S. Pat. No. 9,567,439 and WO2015123552A1.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A composite material comprising:
   at least about 50 wt % sulfur derived from elemental sulfur ($S_8$); and
   about 5-50 wt % tungsten sulfide ($WS_2$);
   wherein the elemental sulfur is heated to a liquid;
   wherein the liquid elemental sulfur and $WS_2$ react to produce the composite material.

2. The composite material of claim 1, wherein $WS_2$ is dispersed in the sulfur.

3. The composite material of claim 1, further comprising about 5-10 wt % of one or more comonomers selected from a group consisting of ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety.

4. The composite material of claim 3, wherein the sulfur and the one or more comonomers form a sulfur copolymer with $WS_2$ dispersed therein.

5. The composite material of claim 3, wherein the one or more comonomers are 1,3-diisopropenylbenzene comonomers.

6. An active material for use in a battery electrode, said active material comprising the composite material of claim 1.

7. An electrochemical cell comprising:
   a. an anode comprising lithium;
   b. a cathode comprising a composite material comprising at least about 50 wt % sulfur derived from $S_8$, and about 5-50 wt % tungsten sulfide ($WS_2$), wherein the elemental sulfur is heated to a liquid, wherein the liquid elemental sulfur and $WS_2$ react to produce the composite material; and
   c. a non-aqueous electrolyte interposed between the cathode and the anode.

8. The electrochemical cell of claim 7, wherein the composite material is capable of generating soluble additive species in-situ upon discharge, wherein the soluble additive species are co-deposited with lower sulfide discharge products onto the cathode by an electrochemical reaction or a non-electrochemical reaction.

9. The electrochemical cell of claim 7, wherein the electrochemical cell has a capacity of about 500 to 1,400 mAh/g.

10. The electrochemical cell of claim 7, wherein in the composite material, $WS_2$ is dispersed in the sulfur.

11. The electrochemical cell of claim 7, wherein the composite material further comprises about 5-10 wt % of one or more comonomers selected from a group consisting of ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety.

12. The electrochemical cell of claim 11, wherein the sulfur and the one or more comonomers form a sulfur copolymer with $WS_2$ dispersed therein.

13. The electrochemical cell of claim 11, wherein the one or more comonomers are 1,3-diisopropenylbenzene comonomers.

14. The electrochemical cell of claim 7, wherein the cathode further comprises an elemental carbon material dispersed in the composite material.

15. A composite material comprising at least about 50 wt % sulfur derived from elemental sulfur ($S_8$), and about 5-50 wt % tungsten sulfide ($WS_2$); wherein the composite material is a vitrified material.

* * * * *